US00PP23617P2

(12) United States Plant Patent
Ikeda et al.

(10) Patent No.: US PP23,617 P2
(45) Date of Patent: May 21, 2013

(54) ***FUCHSIA* PLANT NAMED 'SANIFMINIHO'**

(50) Latin Name: *Fuchsia×hybrida*
Varietal Denomination: Sanifminiho

(75) Inventors: Mito Ikeda, Hyogo (JP); Hidefumi Funakoshi, Hyogo (JP); Yasuo Kishimoto, Hyogo (JP); Tetsuya Kako, Shiga (JP); Yasuyuki Murakami, Shiga (JP)

(73) Assignees: Suntory Flowers Limited, Tokyo (JP); Nishinomiya City, Hyogo (JP)

( * ) Notice: Subject to any disclaimer, the term of this patent is extended or adjusted under 35 U.S.C. 154(b) by 0 days.

(21) Appl. No.: 13/317,904

(22) Filed: Oct. 31, 2011

(51) Int. Cl.
*A01H 5/00* (2006.01)

(52) U.S. Cl.
USPC ..... Plt./300

(58) Field of Classification Search ..... Plt./300
See application file for complete search history.

*Primary Examiner* — Annette Para
(74) *Attorney, Agent, or Firm* — C. A. Whealy

(57) ABSTRACT

A new and distinct cultivar of *Fuchsia* plant named 'Sanifminiho', characterized by its compact, upright and mounding growth habit; freely branching and bushy plant habit; white-colored flowers; freely flowering habit; long flowering period; and relative tolerance to low and high temperatures.

1 Drawing Sheet

Botanical designation: *Fuchsia×hybrida*.
Cultivar denomination: 'SANIFMINIHO'.

BACKGROUND OF THE INVENTION

The present invention relates to a new and distinct cultivar of *Fuchsia* plant botanically known as *Fuchsia×hybrida* and hereinafter referred to by the name 'Sanifminiho'.

The new *Fuchsia* plant is a product of a planned breeding program conducted by the Inventors in Nishinomiya, Hyogo, Japan. The objective of the breeding program is to create new mounding and freely branching *Fuchsia* cultivars with numerous flowers and attractive flower color.

The new *Fuchsia* plant originated from a cross-pollination made by the Inventors in 2004 in Nishinomiya, Hyogo, Japan of a proprietary selection of *Fuchsia×hybrida* identified as code number auf2, not patented, as the female, or seed, parent with a proprietary selection of *Fuchsia×hybrida* identified as code number auq9, not patented, as the male, or pollen, parent. The new *Fuchsia* plant was discovered and selected by the Inventor as a single flowering plant within the progeny of the stated cross-pollination in a controlled greenhouse environment in Nishinomiya, Hyogo, Japan in October, 2007.

Asexual reproduction of the new *Fuchsia* plant by terminal cuttings in a controlled environment in Nishinomiya, Hyogo, Japan and Higashiomi, Shiga, Japan since November, 2007, has shown that the unique features of this new *Fuchsia* plant are stable and reproduced true to type in successive generations.

SUMMARY OF THE INVENTION

Plants of the new *Fuchsia* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'Sanifminiho'.

These characteristics in combination distinguish 'Sanifminiho' as a new and distinct *Fuchsia* plant:

1. Compact, upright and mounding growth habit.
2. Freely branching and bushy plant habit.
3. White-colored flowers.
4. Freely flowering habit; long flowering period.
5. Relatively tolerant to low and high temperatures.

Plants of the new *Fuchsia* differ primarily from plants of the female parent selection in the following characteristics:

1. Plants of the new *Fuchsia* have shorter sepals than plants of the female parent selection.
2. Plants of the new *Fuchsia* and the female parent selection differ in flower color as plants of the female parent selection have purple violet and light pink bi-colored flowers.

Plants of the new *Fuchsia* differ primarily from plants of the male parent selection in the following characteristics:

1. Plants of the new Petunia are more upright than and not as mounding as plants of the male parent selection.
2. Plants of the new *Fuchsia* have single flowers whereas plants of the male parent selection have semi-double flowers.
3. Plants of the new *Fuchsia* and the male parent selection differ in flower color as plants of the male parent selection have pink-colored flowers.

Plants of the new *Fuchsia* can also be compared to plants of 'Sanifhoho' disclosed in U.S. Plant Pat. No. 20,784. In side-by-side comparisons conducted in Nishinomiya, Hyogo, Japan, plants of the new *Fuchsia* and 'Sanifhoho' differed in the following characteristics:

1. Plants of the new *Fuchsia* were more upright than and not as mounding as plants of 'Sanifhoho'.
2. Plants of the new *Fuchsia* had smaller leaves than plants of 'Sanifhoho'.
3. Leaf margins of plants of the new *Fuchsia* were serrate whereas leaf margins of plants of 'Sanifhoho' were entire.

4. Plants of the new *Fuchsia* had smaller and shorter flowers than plants of 'Sanifhoho'.

BRIEF DESCRIPTION OF THE PHOTOGRAPHS

The accompanying colored photographs illustrate the overall appearance of the new *Fuchsia* showing the colors as true as it is reasonably possible to obtain in colored reproductions of this type. Colors in the photographs may differ slightly from the color values cited in the detailed botanical description which accurately describe the colors of the new *Fuchsia*.

The photograph at the top of the sheet comprises a side perspective view of a typical flowering plant of 'Sanifminiho' grown in a container.

The photograph at the bottom of the sheet is a close-up of a typical flowering plant of 'Sanifminiho'.

DETAILED BOTANICAL DESCRIPTION

The aforementioned photographs and following observations, measurements and values describe plants grown in 18-cm containers in a polyethylene-covered greenhouse in Nishinomiya, Hyogo, Japan and under cultural practices typically used in commercial *Fuchsia* production. During the production of the plants, day temperatures ranged from 15° C. to 32° C. and night temperatures ranged from 10° C. to 25° C. Plants were twelve months old when the photographs and the description were taken. In the following description, color references are made to The Royal Horticultural Society Colour Chart, 2001 Edition, except where general terms of ordinary dictionary significance are used.

Botanical classification: *Fuchsia×hybrida* 'Sanifminiho'.

Parentage:

*Female, or seed, parent*.—Proprietary selection of *Fuchsia×hybrida* identified as code number auf2, not patented.

*Male, or pollen, parent*.—Proprietary selection of *Fuchsia×hybrida* identified as code number auq9, not patented.

Propagation:

*Type*.—By terminal cuttings.

*Time to initiate roots, summer*.—About one to two weeks at temperatures of 20° C. to 25° C.

*Time to initiate roots, winter*.—About two to three weeks at temperatures of 15° C. to 20° C.

*Time to produce a rooted young plant, summer*.—About three weeks at temperatures of 20° C. to 25° C.

*Time to produce a rooted young plant, winter*.—About 30 days at temperatures of 15° C. to 20° C.

*Root description*.—Fine, fibrous; yellowish white in color.

*Rooting habit*.—Freely branching; medium density.

Plant description:

*Plant and growth habit*.—Compact, upright and mounding plant habit; freely branching habit with lateral branches developing potentially at every node; bushy plant habit; vigorous growth habit.

*Plant height*.—About 35 cm.

*Plant diameter*.—About 25 cm.

Lateral branch description:

*Length*.—About 15 cm.

*Diameter*.—About 1.7 mm.

*Internode length*.—About 2.4 cm.

*Strength*.—Strong.

*Aspect*.—Initially upright to outwardly arching.

*Texture*.—Pubescent.

*Color*.—Close to 149D; occasionally lightly tinted with close to 187A.

Foliage description:

*Arrangement*.—Opposite, simple.

*Length*.—About 3 cm.

*Width*.—About 2 cm.

*Shape*.—Ovate.

*Apex*.—Acute.

*Base*.—Obtuse.

*Margin*.—Serrate.

*Texture, upper and lower surfaces*.—Sparsely pubescent.

*Venation pattern*.—Pinnate; reticulate.

*Color*.—Developing leaves, upper surface: Close to 144A. Developing leaves, lower surface: Close to 141C. Fully expanded leaves, upper surface: Close to 139B; venation, close to 139B. Fully expanded leaves, lower surface: Close to N144A; venation, close to N144A.

*Petiole*.—Length: About 1.1 cm. Diameter: About 1 mm. Texture, upper and lower surfaces: Smooth, glabrous. Color, upper and lower surfaces: Close to 142A tinted with close to 187A.

Flower description:

*Flower arrangement and habit*.—Single axillary flowers; flowers pendulous; freely flowering habit with potentially two flowers per leaf axil.

*Fragrance*.—None detected.

*Natural flowering season*.—Long flowering period; in Japan, plants flower from spring to autumn; flowering continuous during this period.

*Flower longevity*.—Flowers last about three to four days on the plant; flowers not persistent.

*Flower diameter*.—About 4 cm.

*Flower height* (*depth*).—About 2.5 cm.

*Flower buds*.—Shape: Drop-like. Length: About 2.2 cm. Diameter: About 1.2 cm. Color: Close to 150D.

*Petals*.—Arrangement: Typically four in a single whorl. Length: About 2 cm. Width: About 1.5 cm. Shape: Obovate. Apex: Truncate. Base: Obtuse. Margin: Entire. Texture, upper and lower surfaces: Smooth, glabrous; satiny. Color:

When opening, upper and lower surfaces: Close to 155A.

Fully opened, upper and lower surfaces: Close to 155A.

*Sepals*.—Arrangement: Calyx star-shaped with four sepals fused at the base. Length: About 2.2 cm. Width: About 8.5 mm. Shape: Oblong. Apex: Acuminate. Base: Obtuse. Margin: Entire. Texture, upper and lower surfaces: Smooth, glabrous; satiny. Color: When opening and fully opened, upper surface: Close to 155D; towards the apex, close to 151B. When opening and fully opened, lower surface: Close to 142D blushed with pink.

*Peduncles*.—Length: About 2 cm. Diameter: About 1 mm. Angle: Arching. Strength: Moderately strong. Texture: Sparsely pubescent. Color: Close to 149C.

*Reproductive organs*.—Stamens: Quantity: Eight per flower. Anther shape: Ellipsoidal. Anther size: About 3 mm by 1.5 mm. Anther color: Close to 150D. Pollen amount: Scarce. Pollen color: Close to 155A. Pistils: Quantity: One per flower. Pistil length: About 3.8 cm. Style color: Close to N155D; towards the apex, close to 62D; towards the base, close to 158A. Stigma shape: Conical. Stigma color: Close to 150C. Ovary color: Close to 143B.

*Seeds and fruits*.—Seed and fruit development have not been observed on plants of the new *Fuchsia*.

Temperature tolerance: Plants of the new *Fuchsia* have relatively good low and high temperature tolerance and have been observed to tolerate temperatures ranging from about −2° C. to about 35° C.

Pathogen/pest resistance: Plants of the new *Fuchsia* have not been observed to be resistant to pests and pathogens common to *Fuchsia*.

It is claimed:

1. A new and distinct *Fuchsia* plant named 'Sanifminiho' as illustrated and described.

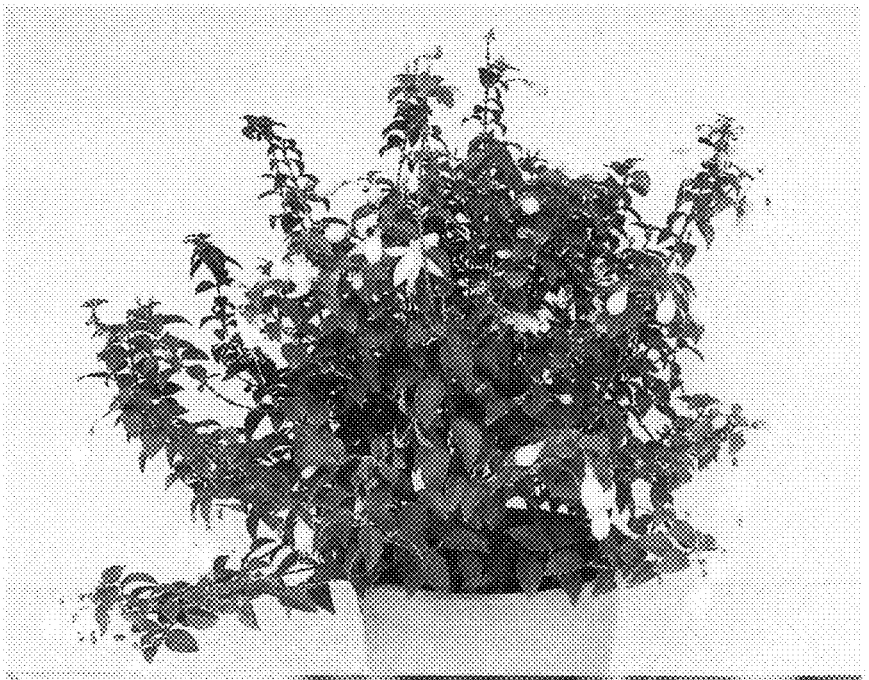
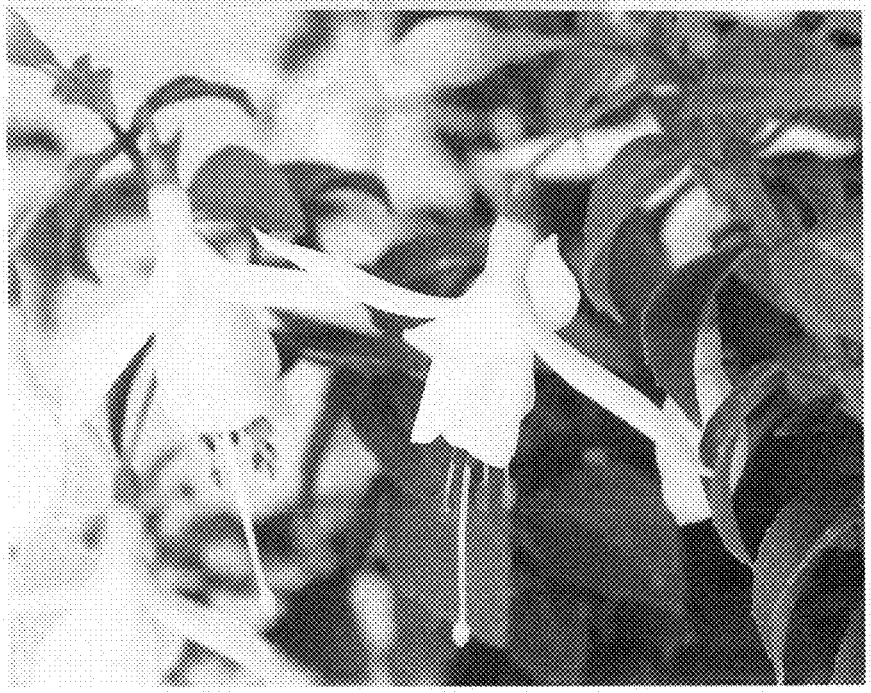

* * * * *